US005115673A

United States Patent [19]

Kline et al.

[11] Patent Number: 5,115,673

[45] Date of Patent: May 26, 1992

[54] NON-DESTRUCTIVE METHOD FOR DETERMINING ELASTIC MODULI OF MATERIAL

[75] Inventors: Ronald A. Kline, Norman, Okla.; Eric I. Madaras, York Town, Va.

[73] Assignees: The United States of America as represented by the United States National Aeronautics and Space Administration, Washington, D.C.; The Board of Regents of the University of Oklahoma

[21] Appl. No.: 556,584

[22] Filed: Jul. 20, 1990

[51] Int. Cl.$^5$ .................... G01N 29/04

[52] U.S. Cl. .................... 73/601; 73/597; 73/602

[58] Field of Search .................... 73/597, 601, 602, 624, 73/627, 787, 798; 250/252.1 R

[56] References Cited

U.S. PATENT DOCUMENTS

| | | | |
|---|---|---|---|
| 4,346,599 | 8/1982 | McLaughlin et al. | 73/597 |
| 4,432,234 | 2/1984 | Jones | 73/597 |
| 4,571,491 | 2/1986 | Vinegar et al. | 250/252.1 R |
| 4,856,341 | 8/1989 | Vinegar et al. | 73/798 |
| 4,899,588 | 2/1990 | Titlow et al. | 73/597 |

OTHER PUBLICATIONS

The Analysis of Fibre-Reinforced Porous Composite Materials by the Measurement of Ultrasonic Wave Velocities—Ultrasonics, Jul. 1978, 5 pages, ©1978 IPC Business Press Ltd.

*Primary Examiner*—Hezron E. Williams
*Assistant Examiner*—Louis M. Arana
*Attorney, Agent, or Firm*—Dunlap, Codding & Lee

[57] ABSTRACT

A non-destructive method for determining elastic moduli of isotropic or anisotropic or homogeneous or non-homogeneous material. The material is subjected to x-radiation for determining the density of the material at a sufficient number of discrete measurement points over the material to create an image of local material density variation. Ultrasonic waves are propagated through the material to determine transit times for each wave at points corresponding to the measurement points. Using the determined density and transit times for each of the measurement points, the elastic moduli at each measurement point is determined. The elastic moduli provides a means for analyzing the mechanical performance of the material. In one aspect, the determined elastic moduli are inputted into a finite element method code for determining mechanical response of the material.

2 Claims, 5 Drawing Sheets

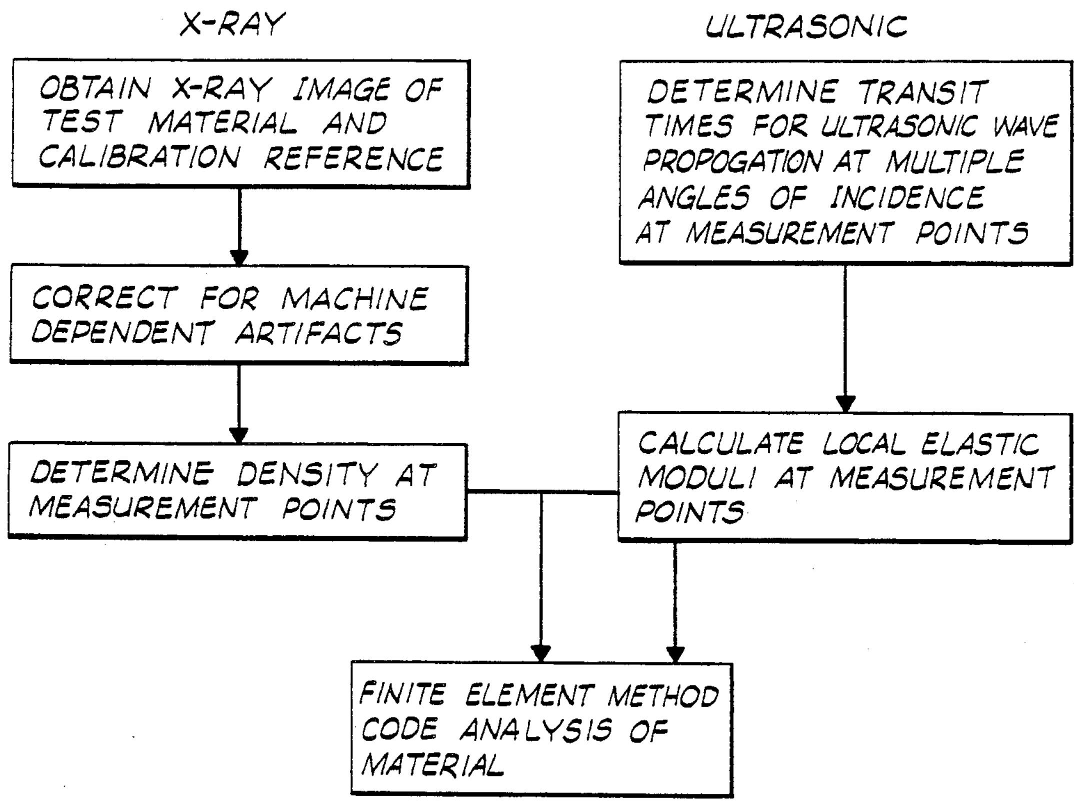
FIG. 1
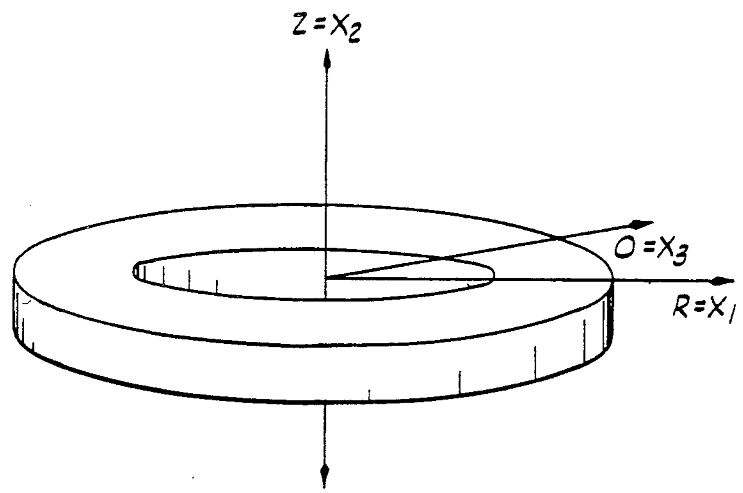
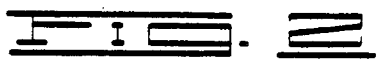

NON-DESTRUCTIVE METHOD FOR DETERMINING ELASTIC MODULI OF MATERIAL

FIELD OF THE INVENTION

The present invention relates generally to a method for determining elastic moduli of material using x-radiation to determine the density of the material at discrete measurement points and ultrasonic waves propagated through the material to determine transit times for each of the measurement points and determining elastic moduli at each of the measurement points from the determined transit times and densities of the respective measurement points.

BRIEF DESCRIPTION OF THE DRAWINGS

FIG. 1 diagrammatically illustrates the method of the present invention.

FIG. 2 is a diagrammatic illustration of a stator coordinate system.

DESCRIPTION OF THE PREFERRED EMBODIMENTS

Figure 3:
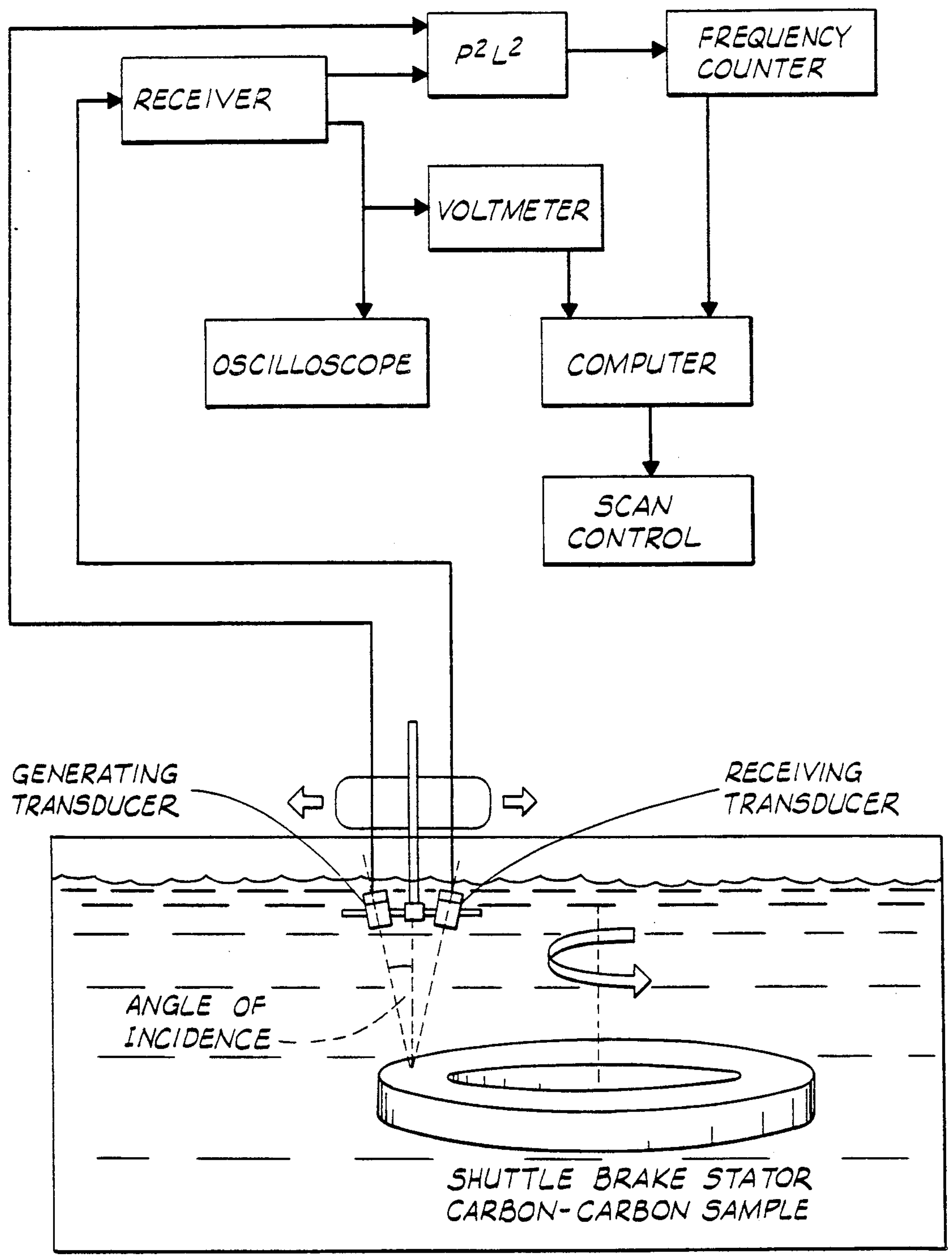
FIG. 3 is a schematic, diagrammatic view of an experimental apparatus used to determine transit times in accordance with the method of the present invention.

The present invention provides a method for analyzing the mechanical performance of isotropic or anisotropic; or homogeneous or nonhomogeneous materials in a non-destructive manner. For example, the method of the present invention provides a means for analyzing the load bearing capability of the material in its service environment.

The method of the present invention generally is illustrated in FIG. 1 of drawings. The material is subjected to x-radiation to produce an image, the image is digitized and the density at a sufficient number of discrete measurement points over the material is determined to substantially create an image of local material density variations. In this x-radiation technique, a calibration reference also is imaged which provides a standard. The image is then corrected for machine dependent artifacts and the density is determined at a sufficient number of discrete measurement points over the material, the number being sufficient to create an image of local material density variations.

Ultrasonic waves are transmitted through the material at multiple angles of incidence. Transit times are determined for each wave at points on the material corresponding to the measurement points. Using the previously determined densities and the transit times, all of the independent elastic moduli at each measurement point then are determined. The elastic moduli then can be used to analyze the mechanical performance of the material.

In one embodiment, the determined elastic moduli for each measurement point are inputted into a finite element method code for determining mechanical response of the material.

It should be noted that the ultrasonic waves propagated through the material in accordance with the method of the present invention can be via through transmission or pulse echo. Further, the x-ray imaging technique can be a two dimensional or a three dimensional type of system. However, the ultrasonic wave portion of the present invention as described herein is limited to a two dimensional analysis.

The use of x-radiation for determining density values at discrete measurement points over a material is well known in the art and a detailed description of the apparatus and methods used in connection with such systems is not deemed necessary. Further, the use of finite element methods and the use of finite element method codes are well known in the art and a detailed description of such methods and codes is not deemed necessary. One such finite element method code suitable for use with the present invention is referred to in the art as "NASTRAN".

The introduction of high strength/low weight composite materials has dramatically changed aircraft design in recent years. And the situation is not static with new materials constantly being introduced along with increased demands on the performance capabilities of composite materials. This is particularly true for emerging aircraft where expected performance requirements exceed the capabilities of currently available materials. While high strength composite materials are commonly utilized for weight critical applications and there are existing materials with elevated temperature capability, there is no accepted material system which combines these two required attributes. In particular, as illustrated in FIG. 1. While carbon-carbon composite structures have been routinely utilized at elevated temperatures, these materials have principally been used as thermal protection rather than as load-bearing structural elements since mechanical properties of conventional carbon-carbon structure will degrade substantially at elevated temperatures, principally due to oxidation. One possible solution to this problem is to employ a thin surface coating to serve as an oxidation barrier. This has led to a new class of carbon-carbon materials which hopefully will preserve the intrinsic performance capabilities of carbon-carbon composites at extreme temperature and offer a possible solution to the material selection problem presented by proposed aircraft designs. The purpose of the present invention is to provide a nondestructive method for characterizing the material properties of these composites.

The governing equations for wave propagation in anisotropic media are relatively straightforward. Linear momentum considerations require that the following ligenvalue equation be satisfied:

$$(\lambda - I)\alpha = 0 \quad (1)$$

where

I = identity matrix $\rho$ = density m = 1 /V = slowness vector l = wave normal

V = phase velocity $\alpha$ = direction cosines of particles displacements the elements of the tensor λ are given by $\lambda_{ik} = c_{ijkl} m_j m_l / \rho$ $$c_{ijkl} = \text{elastic stiffness tensor} \quad (2)$$

Next, one must find the waves which must be generated to satisfy the boundary conditions at the interface between the two media. Continuity of particle displacement and surface traction at the interface requires the typical case):

$$u^{in} + \sum_{i=1}^{3} (u^{re})_i = \sum_{i=1}^{3} (u^t)_i \quad (3)$$

and $$_{in}t^{in} + \sum_{i=1}^{3} t^{re} = \sum_{i=1}^{3} t^t \quad (4)$$

where:

$t = \alpha \nu$ v = normal to interference (direction cosines)

The superscripts in, re, and t correspond to the incident, reflected and transmitted waves and the subscript i = 1, 2, 3 corresponds to the three possible reflected and transmitted waves. Assuming plane wave propagation of the form:

$$i(k_j l_j x - \omega t) \quad (5)$$

$$u_j = A_o a_j e^{i(k(l_j x_j - \omega t))}$$

for each of the incident waves as well as transmitted and reflected waves, it can be shown that the boundary conditions are satisfied providing the frequencies of the waves are equal and Snell's law holds. Numerical procedures have been developed to solve this problem for the reflected and transmitted amplitudes and velocities.

Based on the above considerations, the nature of ultrasonic waves generated at a particular incident angle may be explicitly determined. One important practical aspect of this problem needs to be discussed, the differences between phase and group velocities. All considerations to this point have been for the phase velocity. However, experimentally one measures group velocity. Therefore, one must employ some means of correcting for the fact that the energy flux vector s (|s| = group velocity) where $$S_j = \frac{C_{ijr-laa}}{\rho v}$$

does not coincide with the phase velocity wave normal 1. However, it can be shown that $$s \cdot l = V$$

Hence, one can directly relate the phase and group velocities if the shape of the slowness surface is known.

For mechanical property measurement, we are particularly concerned about wave speed (or transit time measurement) as all pertinent information regarding the elastic moduli ($C_{ijkl}$) may be obtained from the phase velocity.

$$\left( \text{velocity in a given direction} = \frac{\sqrt{\text{moduli}}}{\text{density}} \right)$$

Since there are 3 possible values for each subscript, this means that 81 distinct measurements are, in principle, needed. However, because of symmetry considerations in the stress and strain tensors as well as energy consideration, it may be argued that $C_{ijkl} = C_{jikl}$ $C_{ijkl} = C_{ijlk}$ and $C_{ijkl} = C_{klij}$ This reduces the number of independent constants from 81 to 21. In order to simplify the calculations, the following index simplification may be employed:

11→1, 22→2, 33→3, 23→4, 13→5, 12→6 so $C_{1111} \rightarrow C_{11}, C_{1112} \rightarrow C_{16}$, etc.

where $C_{in}$ now represents a 6×6 symmetric array whose elements represent the various elastic stiffness associated with the material. Internal symmetry allows further reduction. For the woven carbon-carbon structure illustrated here (assuming orthotropy with the radial and tangential directions being the two in-plane orthotropic axes) considered here, there are 9 pertinent elastic moduli to be determined ($C_{11}$, $C_{22}$, $C_{33}$, Chd 12, $C_{13}$, $C_{23}$, $C_{44}$, $C_{55}$ and $C_{66}$; see FIG. 2 for coordinate system). Note that direction 1 corresponds to this tangential direction, 2 represents the through thickness direction, and 3 the radial direction.

Thus, 9 independent measurements must be made. One choice is a longitudinal wave traveling normal to fiber reinforcement plane. This yields $C_{22}$ directly. Propagation of shear waves in a direction normal to the surface could be used to measure $C_{55}$ and $C_{13}$ directly. Unfortunately, coupling problems associated with shear wave propagation preclude efficient scanning. Since access often is available only to one of the panel surfaces, mode conversion is the preferred approach. This brings oblique incidence and energy flux consideration into play as the energy flux vector will, in general, deviate from the wave normal unless the propagation direction is a 2-, 4-, or 6-fold symmetry axis or perpendicular to a plane of material symmetry (as appropriate for all waves generated by normal incidence in a symmetric composite laminate). However, as demonstrated above, these considerations can be efficiently included in the data analysis. One must simply choose appropriate angles for the measurement of the 9 moduli.

Figure 4A:
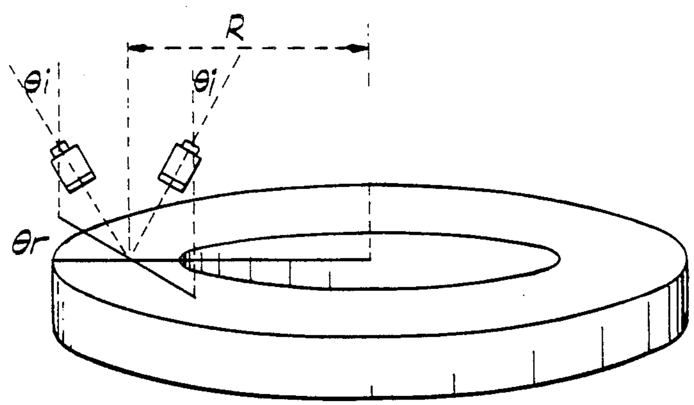
FIG. 4A-B is a diagrammatic, schematic view of transducer orientations used for scans in an experimental test of the methods of the present invention.
Figure 4B:
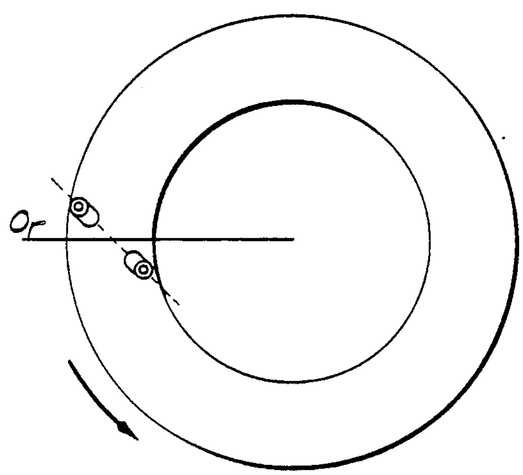

Ultrasonic velocity measurements were carried out using the apparatus illustrated in FIG. 3. Test geometry is illustrated in FIG. 4. The transducers were mounted in a fixture attached to a computer-driven scanning bridge which allowed the transducer assembly to be indexed both radially and tangentially (angular displacement). Transducer angle of incidence was fixed in a separate jig for each angle of interest. The transducer-specimen distance was also adjusted for each angle to insure that the sensing transducer would receive the desired ultrasonic reflections (front surface and back surface). Separate scans were performed for each inspection angle. (Note: To increase inspection speed, it may be desirable to make all 9 measurements for a given point in a single pass. This can be readily achieved by incorporating motion control including one rotation angle for each transducer.) Inspection angles were chosen to take optimal advantage of the assumed orthotropic symmetry of the material. First, a normal incidence longitudinal phase velocity inspection was performed. This yields $C_{22}$ directly as $V_L=\sqrt{C_{22}/\rho}$ for this mode of propagation. Next, three-phase velocities were measured with the transducers aligned in the tangential direction and incidence angles of 5° (QL wave), 15° (QT wave) and 20° (QT wave). This produces three nonlinear equations involving unknowns $C_{11}$, $C_{12}$ and $C_{66}$. Repeating the same procedure with the transducers aligned in the radial direction produces three coupled nonlinear equations which can be solved for $C_{33}$, $C_{44}$ and $C_{23}$. The remaining two moduli ($C_{13}$ and $C_{55}$) were determined using QT phase velocity measurements and inspection angles at 15° and 20° with the transducers oriented at 45° with respect to radial.

The approach to characterizing C—C microstructure was based on ultrasonic velocity measurements. However, since as just shown, ultrasonic velocity measurements are sensitive to both elastic moduli and density in order to characterize the elastic anisotropy, it was necessary to have an additional local measure of density. In this case, radiographic test methods were employed for this purpose. A schematic of the test methodology is shown in FIG. 4 and the test procedure followed is presented below.

Ultrasonic testing was performed in immersion on a full-sized sample space shuttle brake stator. In order to prevent moisture absorption during the inspection process, the samples were sprayed with an acrylic coating layer. The layer was sufficiently thin that it could be safely neglected in the time-delay measurements. For oblique incidence, a set of specially designed test fixtures were fabricated for pulse-echo inspection at fixed angles of incidence. The inspection was performed by mounting the specimen on a turntable which allowed rotation of the ring in 1.2° increments. The scan equipment also permitted radially indexing the fixture in 0.5 cm increments. In this way, it was possible to scan the part. It should, however, be pointed out that due to the use of oblique incidence, only the center region of the ring could be reliably inspected due to edge effects. This problem, of course, increases with increasing angle of incidence. In experiments, maximum angle of incidence of 20° was used which permitted inspection to within a distance on the order of the part thickness from the part's edges.

One of the major problems encountered in this research effort was the high degree of attenuation and dispersion present in the sample. The resulting signal distortion due to a variety of effects including porosity and scattering from the reinforcing fibers, makes ultrasonic velocity testing rather difficult. As signal distortion is highly dependent upon frequency, to reduce distortion errors in the velocity measurements, relatively low frequency (500 kHz) narrow band sensors were used because of the thickness and attenuation of the sample. This coupled with the use of a sensitive pulsed phase locked loop ($P^2L^2$) detection circuit, reduced dispersion errors considerably and made accurate velocity measurements possible.

Radiographic test methods were used for local density determination in the composite samples. For this measurement, radiographs of the complete stator were made along with an x-ray image of an aluminum calibration bar (stepped in increments of 0.05 inch).

To accomplish this, it was first necessary to convert the photographic x-ray images to digital form. This was done using an Eiconiz digitizing camera at NASA/Langley with 8-bit resolution. It should be pointed out that the limited field of view of the digitizing camera along with the size of the stator (since it was full-size image) precluded coverage of the entire part with a single shot. Accordingly, multiple images were made and later merged together into a single image. It also should be noted that the light source for the digitizing camera was not uniform, hence altering the x-ray intensity. In order to correct this problem, it was necessary to first digitize an image of the light source itself and develop normalizing factors to adjust each point in the image to a constant intensity level. These same correction factors were then used to correct the digitized radiographic images for the light intensity variations.

Another problem arose from the fact that the x-ray absorption values for C—C composites are not well established and had to be determined. To do this, we used a C—C calibration sample where the density could be readily determined which was radiographed along with the stator and Al stepped wedge. By comparing the C—C calibration block to the Al sample, the absorption coefficient for C—C could be directly established.

Figure 5:
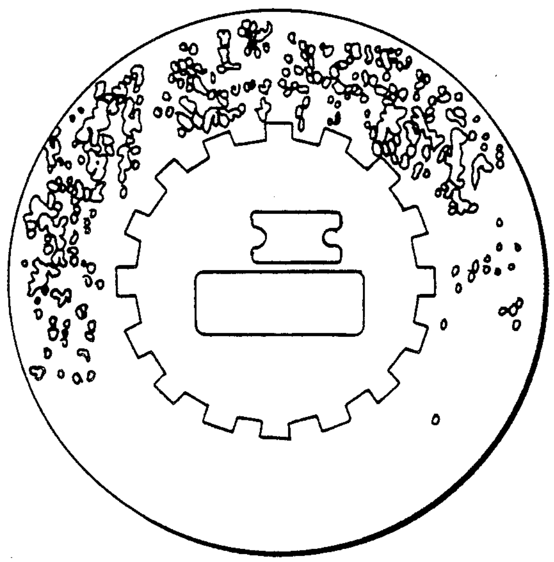
FIG. 5 is an image showing local density variations in a material and a standard or calibration reference.

Density variations, as measured using the radiographic test method previously described, are illustrated in FIG. 5. Density variations on the order of ±10% of this average value were observed. Typically, slightly higher measured densities were observed along the inner and outer radii of the part. The origin of this finding has not been established, although it may be indicative of more complete densification at the part extremities during the chemical vapor deposition process.

Figure 6:
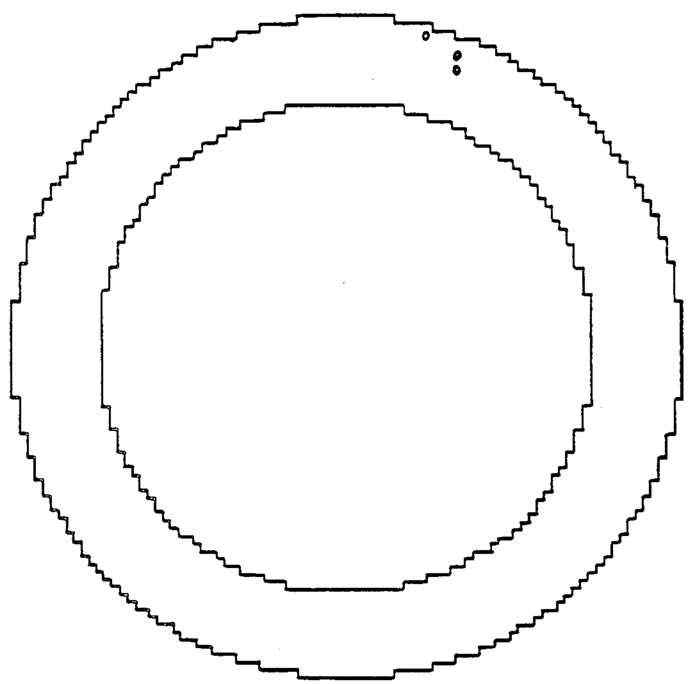
FIG. 6 represents the experimental results for the elastic moduli (see $C_{11}$ vs position).
Figure 7:
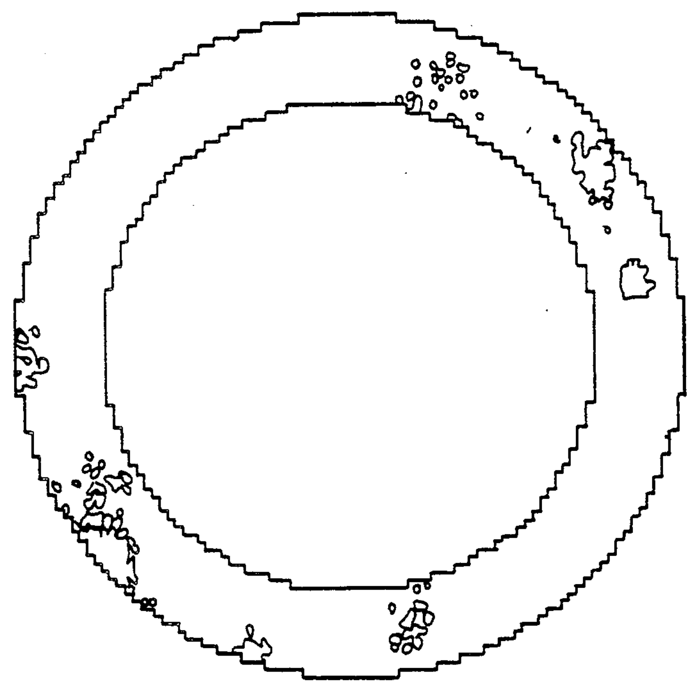
FIG. 7 represents the experimental results for the elastic moduli (see $C_{22}$ vs position).
Figure 8:
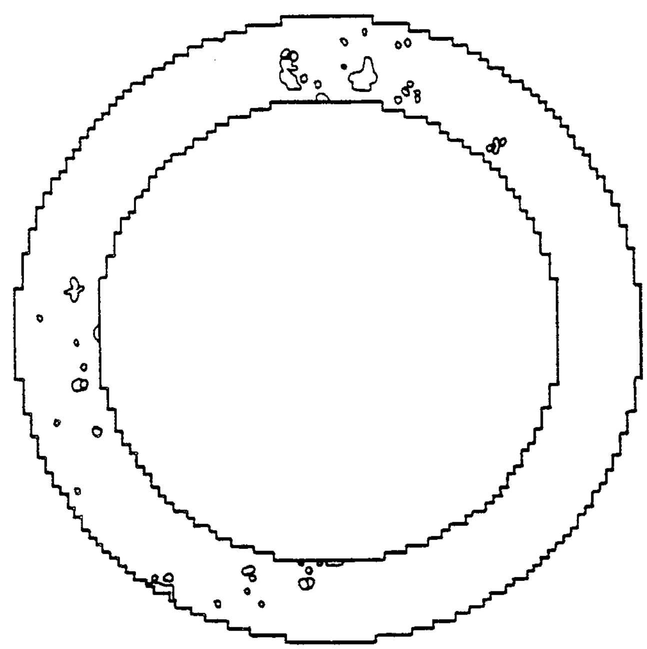
FIG. 8 represents the experimental results for the elastic moduli (see $C_{33}$ vs position).

The results from the local phase velocity measurements at multiple angles of incidence and the density determination were analyzed using the technique described earlier to determine the anisotropic elastic properties of the material and how these properties varied from position to position While all nine orthotropic moduli were determined, three are presented in FIGS. 6–8. Of these measurements, the most reliable is the through thickness modulus ($C_{22}$) determination as only one measurement is required (through thickness time delay) and the desired modulus can be obtained directly (not through numerical analysis techniques as required for the remaining moduli). Accordingly, the variation in this measurement is somewhat less than that found for all the remaining moduli, and significantly less than that observed for the two in plane moduli ($C_{13}$ and $C_{55}$) which involve all seven of the other moduli (previously determined) in their calculation. Some degree of error propagation is inherent in this approach and further study is needed to ascertain the accuracy of the velocity and density measurement techniques utilized and the ultimate effect of this measurement uncertainty on the moduli calculations.

Upon examination of the results, one finds that the ultrasonic results have much in common with the x-ray density measurements. One of the most prominent features of the x-ray scan is a low density region near the top of the scan. This feature can be observed in virtually all of the $C_{ij}$ plots as a region of significantly lower modulus than the surrounding materials. This is supportive of the conjecture that incomplete densification has taken place in this region. A second possibility is an increased microcrack density in this region as this type of microstructural flaw would result in lower density as well as decreased moduli (particularly in-plane). There are, however, other regions which exhibit somewhat different behavior. Consider, for example, the anomalous region in the center of the ring at the 75° position with respect to vertical in the Figure This area does not appear to be significantly different from the surrounding media from the x-ray results yet modulus measurements are, in fact, dissimilar. Of particular note is the observation that while some of the properties are degraded in this region, others are improved. The in-plane normal stiffness ($C_{11}$, $C_{33}$) are lowered in this region while the out-of-plane stiffness properties ($C_{22}$) are enhanced. Possible explanations for this is a warping of the prepreg fabric during layup or fiber breakage in the region. While it is not possible to test the accuracy of these assertions without sectioning the sample, it is clear that multiple ultrasonic modulus measurements do provide a direct method of characterizing local variation in material microstructure. With additional experience in interpreting the results, we may be able to precisely nondestructively classify material anomalies and their origin in carbon-carbon samples.

Figure 9:
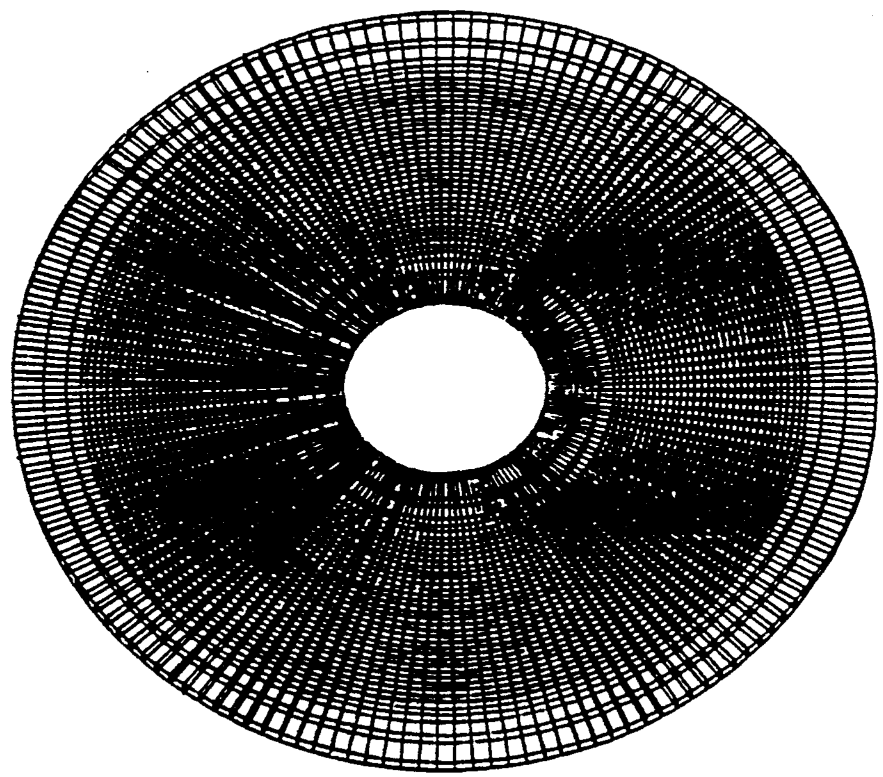
FIG. 9 represents the finite element mesh applied to the stator geometry (see Finite Element Mesh-Stator).

Structural analysis was performed on the brake ring using the finite element method (FEM) using the measured local stiffness as inputs into the model. The finite element mesh for the carbon-carbon composite brake disk is shown in FIG. 9. The disk was modeled with 10800 nodal points and 5250 HEXA elements and was analyzed using MSC/NASTRAN Version 65B2 run on an IBM 3081K mainframe.

The brake disk was subjected to diametric compression. This was modeled by fixing the disk in the r and theta directions at two grid points (one on each of the upper and lower surfaces) along the outer edge of the disk. Then a force was applied radially inward to the grid points on the upper and lower surfaces along the outer edge at the point 180 degrees from the fixed nodes, the magnitude of this force was 5000 pounds, distributed equally between the two grid points. This distribution was chosen to keep the outer surface of the disk as near as parallel as possible with the x axis. For stability purposes, it was also necessary to fix the grid points in the theta direction at the points where the force was applied. This analysis was repeated for similar loading and boundary conditions rotated by 36, 72, 90, 108 and 144 degrees counterclockwise from the original case.

For each of the loading cases, the output generated by NASTRAN included the displacement and the normal stresses and strains in the r, theta, and x directions, as well as the shear stresses and strains in the r-theta plane. Also output were the strain energy and strain energy density for each element. In order to compare our results with those for an homogeneous carbon-carbon disk, another analysis was run for a disk with the same geometry, loading and boundary conditions. However, for this disk, the stiffness matrix components were constant throughout the disk. This analysis allowed us to better visualize the effects of material inhomogeneity on the stress/strain distribution.

Using the procedure outlined above, the local densities and elastic stiffness were determined for the space shuttle stator. Typical results are illustrated in FIG. 7 where the through thickness normal stiffness is shown. Of particular interest is the low stiffness regions near the top of the Figure. Typical variations in moduli were 10%. These results were used as inputs to the NASTRAN finite element code. This allows one to analyze the response of a model with actual, not idealized, mechanical properties.

Changes may be made in the construction and the operation of the various components, elements and assemblies described herein without departing from the spirit and scope of the invention as defined in the following claims.

What is claimed is:

1. A non-destructive method for determining elastic moduli of an isotropic or anisotropic or homogenous or nonhomogeneous material, comprising:

subjecting the material to x-radiation to produce an image, digitizing the image and determining density at a sufficient number of discrete measurement points over the material to substantially create an image of local material density variations;

propagate ultrasonic waves through the material at multiple angles of incidence and determine transit times for each wave at points corresponding to the measurement points; and determining for each measurement point all of the independent elastic moduli at each measurement point using the densities determined by subjecting the material to x-radiation and the transit times determined by propagating ultrasonic waves through the material.

2. The method of claim 1 further comprising:

inputting the elastic moduli for each measurement point into a finite element method code for determining mechanical response of the material.

* * * * *

UNITED STATES PATENT AND TRADEMARK OFFICE
CERTIFICATE OF CORRECTION

PATENT NO. : 5,115,673

DATED : May 26, 1992

INVENTOR(S) : Kline, et al.

It is certified that error appears in the above-identified patent and that said Letters Patent is hereby corrected as shown below:

Column 2, line 59, delete the word "ligenvalue" and substitute therefore the words --eigen value--.

Column 3, line 9, add the letter --(u)-- between the words, displacement, and, and.

Column 3, line 9, add the letter --(t)-- between the words, traction, and, at.

Column 3, line 9, add the letter --(for-- between the words, requires, and, the.

Column 4, line 26, the characters "Chd 12" should be --$C_{12}$--.

Column 7, line 4, a --.-- should be between the words, Figure, and, This.

Signed and Sealed this

Third Day of August, 1993

Attest:

MICHAEL K. KIRK

Attesting Officer

Acting Commissioner of Patents and Trademarks